United States Patent [19]

Bastyr et al.

[11] Patent Number: 5,292,303
[45] Date of Patent: Mar. 8, 1994

[54] HINGED ORTHOPEDIC BRACE HAVING AN ADJUSTABLE PIVOT RANGE

[75] Inventors: Charles A. Bastyr; David B. Winer, both of San Diego, Calif.

[73] Assignee: Smith & Nephew Donjoy, Inc., Carlsbad, Calif.

[21] Appl. No.: 907,480

[22] Filed: Jul. 1, 1992

[51] Int. Cl.5 .............................................. A61F 5/00
[52] U.S. Cl. ........................................ 602/16; 602/26
[58] Field of Search ................... 602/5, 16, 20, 23, 26, 602/27

[56] References Cited

U.S. PATENT DOCUMENTS

| 401,933 | 4/1889 | De Camp | 602/16 |
|---|---|---|---|
| 3,902,482 | 9/1975 | Taylor . | |
| 4,054,130 | 10/1977 | Franke | 602/16 |
| 4,340,041 | 7/1982 | Frank | 602/16 |
| 4,397,308 | 8/1983 | Hepburn | 602/16 |
| 4,481,941 | 11/1984 | Rolfes . | |
| 4,489,718 | 12/1984 | Martin | 602/16 |
| 4,531,515 | 6/1985 | Rolfes . | |
| 4,599,998 | 7/1986 | Castillo . | |
| 4,955,369 | 9/1990 | Bledsoe et al. | 602/16 |
| 4,982,732 | 1/1991 | Morris . | |
| 5,000,169 | 3/1991 | Swicegood et al. | 602/16 |
| 5,002,044 | 3/1991 | Carter | 602/16 |
| 5,062,858 | 11/1991 | Broeck et al. | 602/16 X |
| 5,078,127 | 1/1992 | Daneman et al. . | |

Primary Examiner—Richard J. Apley
Assistant Examiner—Linda C. M. Dvorak
Attorney, Agent, or Firm—Rodney F. Brown

[57] ABSTRACT

An orthopedic brace is provided which includes a pair of arms joined by a hinge about which the arms pivot relative to each other. The brace also includes pins for adjustably limiting the pivot range of the arms, members for retaining the pins in operable position during use of the brace and for retaining the pins in pivotal connection with the brace during repositioning of the pins, and a cover with a lid thereon for selectively accessing the pins and enabling repositioning of them as desired.

16 Claims, 4 Drawing Sheets

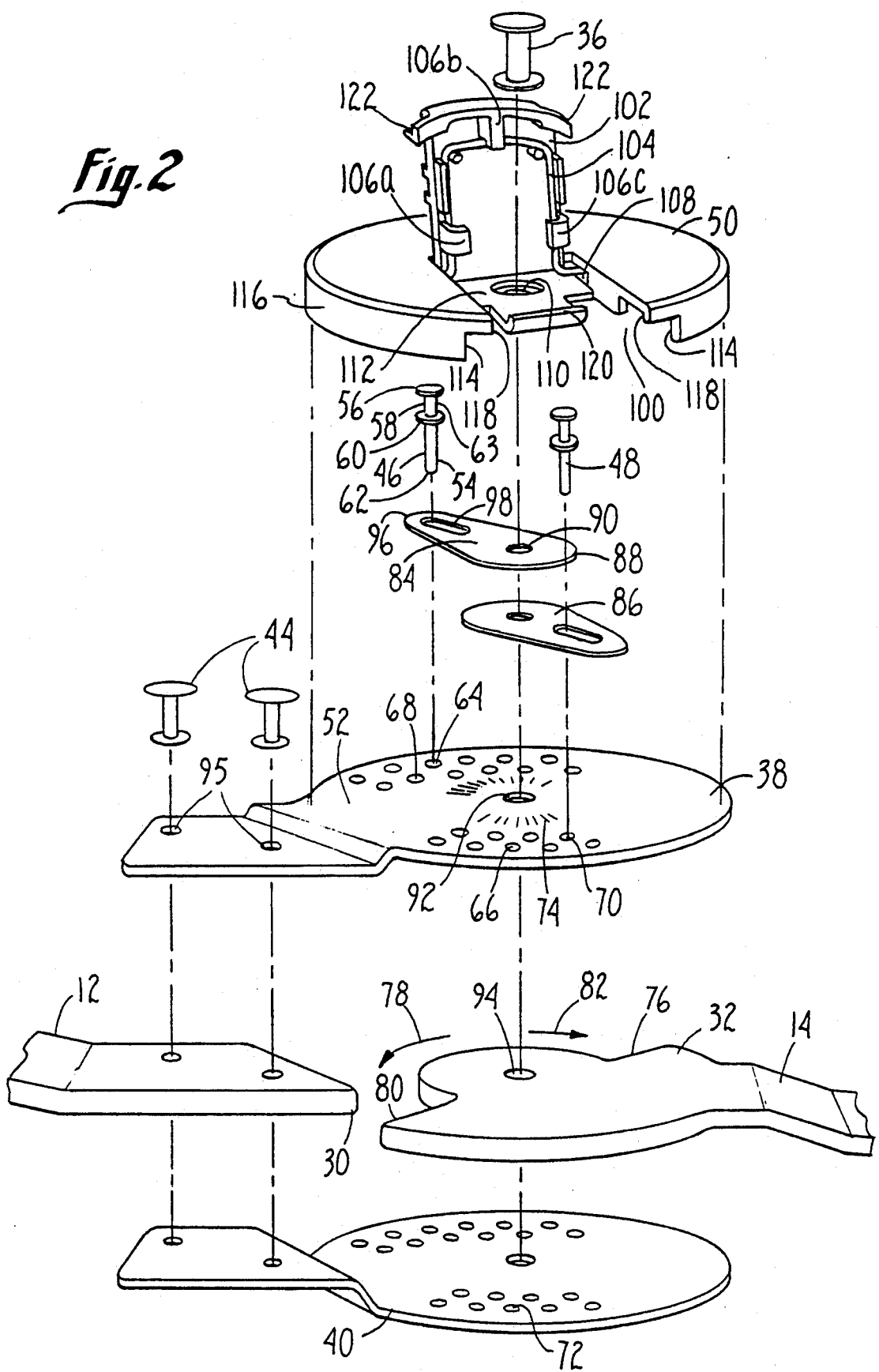

HINGED ORTHOPEDIC BRACE HAVING AN ADJUSTABLE PIVOT RANGE

TECHNICAL FIELD

The present invention relates generally to orthopedic braces, and more particularly to an orthopedic brace having a hinge with an adjustable range of pivotal movement.

BACKGROUND OF THE INVENTION

Hinged orthopedic braces having an adjustable range of pivotal movement, as disclosed by U.S. Pat. Nos. 4,481,941 and 4,531,515, both to Rolfes, are known in the art. The braces disclosed therein have stops positioned at points about the hinge to limit the range of pivotal movement of the two arms of the brace relative to each other which are joined at the hinge. The stops, as taught by the art, may be a pin or a screw, although screws are preferred because, being threaded, they can be firmly secured to the brace by corresponding threads in the brace until it is desired to reposition them.

It has been found, however, that screws of the sizes required for use as stops in hinged braces are so small as to render removal and repositioning of the screws in different positions about the hinge awkward and cumbersome. Thus, screws act as a hindrance to necessary adjustments of the brace, particularly by an unskilled user. The small size of the screws also renders them susceptible to being misplaced or lost during adjustment of the brace. Pins are even less satisfactory than screws as stops because of their propensity to slip out of position during use of the brace. As such, a brace is needed which overcomes these problems experienced in the prior art.

Accordingly, it is an object of the present invention to provide a hinged orthopedic brace having stops which effectively limit the range of pivotal movement of the two brace arms, yet which are easily repositionable on the brace to adjust the range of pivotal movement of the arms with a minimal risk of losing or misplacing the stops. It is further an object of the present invention to provide a hinged orthopedic brace having such stops which resist inadvertent slippage from their operable position during use of the brace. It is yet another object of the present invention to provide a hinged orthopedic brace having stops which are selectively accessible to the user, thereby enabling or restricting repositioning of the stops as desired.

SUMMARY OF THE INVENTION

The present invention is an orthopedic brace comprising a pair of arms joined by a hinge about which the arms pivot relative to each other. The brace further comprises means for adjustably limiting the pivot range of the arms, means for retaining the limiting means in operable position during use of the brace and for retaining the limiting means in pivotal connection with the brace during repositioning of the limiting means, and means for selectively accessing the limiting means to enable or restrict repositioning thereof as desired.

The brace is mounted on the body of a user patient such that the hinge is positioned substantially adjacent to the skeletal joint of the user which is being supported by the brace. The arms extend in opposite directions away from the hinge. Each arm has one or more support members, such as adjustable straps, which are attached proximal to the end of the arm opposite the hinge or at intermediate points therebetween to fixably engage the body of the user. The hinge end of the first arm is configured in the shape of a flat plate extending longitudinally from the arm. The plate has a plurality of spaced-apart holes formed therethrough in an arranged pattern. The hinge end of the second arm fits behind the plate and a pivot pin passes through an aperture provided in the plate and in the end of the second arm to pivotally retain the two arms and form the hinge.

The limiting means comprises at least one limiting pin sized to be received by the holes through the plate, the holes being arranged about the pivot pin. When positioned in one of the holes, the limiting pin extends behind the plate to block further pivoting movement of the second arm in a given direction. The limiting pin can be selectively placed in a particular hole to establish the desired range of flexion or extension of the skeletal joint. Furthermore, the range of flexion or extension can be modified by repositioning the limiting pin in a different hole.

By placing two limiting pins in two different predetermined holes of the plate, the present invention can limit pivoting movement of the second arm in both directions. Accordingly, one limiting pin is selectively placed in one hole of the plate in the manner set forth above to establish the desired range of flexion for the skeletal joint and the other limiting pin is positioned in a different hole of the plate to establish a desired range of extension for the skeletal joint.

The limiting pins are cylindrically shaped and provided with a smooth surface to readily slide into or out of the smooth rounded holes of the plate, the holes being slightly larger in diameter than the limiting pins. The means for retaining the limiting pins is a member formed from a strip of flexible material having a flattened elongated configuration. The flexible retention member engagingly extends from one of the limiting pins across the top of the plate to the pivot pin, thereby retaining the limiting pin in pivotal connection with the brace even when the limiting pin is removed from one of the holes in the plate during adjustment of the brace.

The retention member has an essentially unstressed linear shape when the limiting pin is positioned within a hole. However, the retention member elastically deforms to a stressed arcuate shape when the limiting pin is withdrawn from a hole during adjustment of the brace, the pivot pin pivotally maintaining one end of the retention member proximal to the plate while the limiting pin maintains engagement with the other end of the retention member even as the limiting pin is disposed away from the plate. As such, the retention means retains the limiting pin in an aligned hole during use of the brace due to its bias in the direction of the plate, while retaining the limiting pin in connection with the brace even when the limiting pin is forcibly removed from a hole during repositioning thereof. Thus, the retention member avoids loss or misplacement of the limiting pin during adjustment of the brace.

The retention member engages the limiting pin through a longitudinal slot provided in the end of the retention member while the opposite end of the retention member pivotally engages the pivot pin. The slot is sized to receive the cylindrical body of the limiting pin. A first widened portion, however, is provided on the cylindrical body of the limiting pin, which has a width larger than the width of the slot, to prevent the limiting pin from sliding entirely through the slot. The first widened portion is located at the end of the limiting pin opposite the holes in the plate such that the retention member is positioned between the plate and the first widened portion when the limiting pin is placed within a hole.

A second widened portion can also be provided on the cylindrical body of the limiting pin spaced below the first widened portion. The second widened portion has a width larger than the diameter of the holes in the plate and larger than the width of the slot, to enable engagement of the limiting pin and retention member between the first and second widened portions of the limiting pin. The length of the slot is greater than the diameter of the body of the limiting pin such that the limiting pin is longitudinally slidable within the slot. As such, the limiting pin can be aligned with different holes in the plate that are at varied radial distances from the pivot pin.

The access means comprises a cover residing over the plate which is provided with an opening that is selectively positionable over the limiting pin at any location on the plate. The opening is fitted with a lid having a closed position and an open position. When the lid is in the closed position, the cover substantially encloses the plate to restrict access to the limiting pin and consequently prevent readjustment of the brace. When the lid is in the open position, it is disposed away from the plate to expose the opening in the cover and enable repositioning of the limiting pin therethrough. The dimensions of the cover relative to the limiting pin are such that even if the retention member fails to retain the limiting pin in place within a particular hole, there is insufficient clearance between the limiting pin and the cover when the lid is in the closed position for the limiting pin to clear the hole before abutting the cover. Thus, the cover acts as a secondary retention means for the limiting pin.

The lid is pivotally connected to the cover by a lid hinge that enables selective repositioning of the lid from the closed to the open position. To reposition the lid in the open position, it is pivoted about the hinge, thereby raising the lid away from the plate to disengage the lid from the opening and enable access to the limiting pin through the opening. A latching mechanism can be provided on the cover to releasably lock the lid to the cover when the lid is in the closed position and prevent inadvertent pivoting of the lid to the open position. The cover is also rotatably connected to the brace to enable rotatable repositioning of the opening over any hole in the plate as the limiting pin is moved from one hole to another.

In a preferred embodiment of the present invention, the hinge end of the first arm is further provided with a second plate corresponding in configuration to the first plate described above. The second plate extends longitudinally from the arm parallel to, but behind, the first plate with a gap formed therebetween. Accordingly, the hinge end of the second arm fits into the gap between the two plates. The second plate has an aperture formed therethrough, into which the pivot pin extends to pivotally retain the second plate in cooperative alignment with the first plate and second arm at the hinge.

Like the first plate, the second plate has a plurality of spaced-apart holes formed therethrough in an arranged pattern such that the holes of the second plate align with the holes of the first plate. In accordance with this configuration, the limiting pin performs in substantially the same manner as described above when extended through a hole of the first plate to block the pivoting movement of the second arm in a given direction. However, the limiting pin extends not only through the hole of the first plate, but also through the corresponding aligned hole of the second plate to provide reinforced support of the limiting pin.

The present invention will be further understood, both as to its structure and operation, from the accompanying drawings, taken in conjunction with the accompanying description, in which similar reference characters refer to similar parts.

BRIEF DESCRIPTION OF THE DRAWINGS

FIG. 2 is an exploded perspective view of the hinged orthopedic brace of the present invention.

DESCRIPTION OF PREFERRED EMBODIMENTS

The hinged brace of the present invention has, in general, substantially the same construction as the hinged braces shown in U.S. Patents to Rolfes, U.S. Pat. Nos. 4,481,941 and 4,531,515, which are incorporated herein by reference. The present invention resides in modifications to the means for adjustably limiting the pivot range of the hinge that are disclosed in the patents to Rolfes, in the addition of retention and access means cooperating with the modified limiting means, and in all such modifications and additions set forth above in combination with the remaining structure of the hinged brace.

Figure 1:
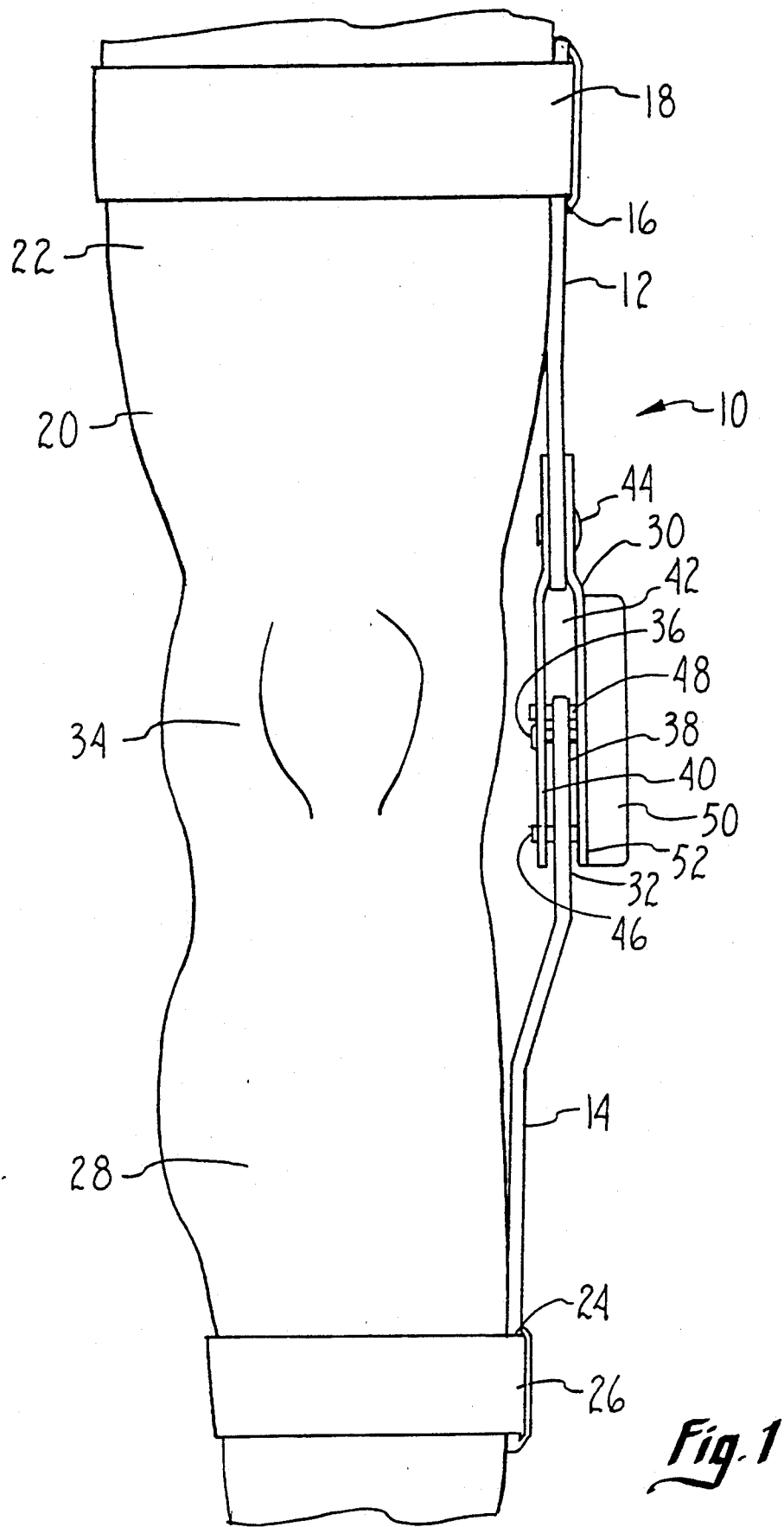
FIG. 1 is a front view of a hinged orthopedic brace of the present invention shown in place on the leg of a user.

Referring initially to FIG. 1, a hinged orthopedic brace of the present invention is shown and generally designated 10. Brace 10 is a knee brace fitted to the left leg of the body for purposes of illustration, although it is understood that one skilled in the art can readily adapt the brace of the present invention to the opposite leg or to other skeletal joints of the body, such as the hip joint, following the instant teaching. Brace 10 comprises an upper or first arm 12 and a lower or second arm 14 both of which are substantially rigid, preferably being formed from a lightweight, but high-strength, metal. First arm 12 has a first end 16 that has a support member in the form of an upper leg strap 18 threadably attached thereto. With brace 10 in place on the left leg 20 of a user as shown in FIG. 1, upper leg strap 18 adjustably engages the upper leg 22 in the region of the femur.

Second arm 14 likewise has a first end 24 that has a support member in the form of a lower leg strap 26 threadably attached thereto. Lower leg strap 26 engages the lower leg 28 in the region of the tibia. It is noted that only one upper leg strap 18 and one lower leg strap 26 are shown attached to first and second arms 12 and 14 respectively. However, a plurality of such straps can be attached to both arms at various points along their length if desired. Adjustable straps 18 and 26 serve to maintain brace 10 in position about the leg 20 in a manner known to one skilled in the art.

First and second arms 12 and 14 have second ends 30 and 32 respectively, which intersect proximal to the knee 34 and are pivotally joined by a pivot pin 36, preferably in the form of a substantially permanent rivet about which arms 12, 14 can pivot. Second end of first arm 30 is configured in the form of two substantially parallel plates 38 and 40. A gap 42 is created between the upper or first plate 38 and the lower or second plate 40 and the second end of second arm 32 fits in gap 42 where it is secured by pivot pin 36 in pivotal connection with plates 38 and 40. Plates 38 and 40 can be integral with first arm 12, but in the present embodiment are shown as being separate components formed from a rigid metal which are fixably attached to first arm 12 by one or more rivets 44.

Flexion and extension limiting pins 46 and 48 are further shown extending through first and second plates 38, 40. The structure and function of limiting pins 46, 48 is described in detail hereafter with reference to subsequent figures. Finally, FIG. 1 discloses a cover 50 rotatably mounted on and enclosing the face 52 of first plate 38. Cover 50 is likewise described in detail hereafter with reference to subsequent figures.

Referring now to FIG. 2, limiting pins 46, 48 and cover 50 are shown in greater detail. Limiting pins 46 and 48 are substantially identical in structure. Accordingly, the structure of either pin is described with reference to limiting pin 46. Limiting pin 46 has an elongated cylindrical body 54 with a substantially smooth surface and a first widened portion 56 at one end of body 58. Limiting pin 46 further has a second widened portion 60 positioned between the other end of body 62 and first widened portion 56, thereby forming an isolated segment of body 63 bounded by first and second widened portions 56 and 60.

A plurality of spaced-apart holes substantially identical in size and having substantially smooth walls are formed through first plate 38 in a pattern of arranged sets, wherein two sets of holes 64 and 66 are at the outer radius of first plate 38 and two sets of holes 68 and 70 are at an inner radius of plate 38. The holes of sets 64 and 6B are termed flexion limiting holes and the holes of sets 66 and 70 are termed extension limiting holes for reasons made apparent hereafter. Second plate 40 likewise has a plurality of spaced-apart holes formed therethrough in the same pattern of arranged sets as first plate 38 such that the holes of the second plate align with the holes of the first plate.

Although obstructed from view in FIG. 2 by first plate 38, second plate 40 has two sets of holes at its outer radius and two sets of holes at an inner radius. The sets of holes in second plate 40 are similarly termed flexion limiting holes and extension limiting holes. Only the extension limiting holes 72 at the outer radius of the second plate are partially visible in FIG. 2, but the remaining sets of holes in second plate 40 align identically with sets 64, 68, 70 respectively, of first plate 38.

Each hole in first plate 38, as well as correspondingly aligned holes in second plate 40, can be identified by radial calibrations 74 provided on the face of first plate 52. Such radial calibrations 74 are used to rapidly measure the flexion or extension limits established by placement of limiting pins 46 and 48 in selected holes of plates 38 and 40. Thus, end 62 of limiting pin 46 is smaller in diameter than the holes of first and second plates 38, 40, thereby enabling the holes to receive end 62. Second widened portion 60, however has a width greater than the diameter of the holes to prevent the segment of the limiting pin 63 from entering any particular hole.

In FIG. 2, flexion limiting pin 46 is shown to be positioned within a flexion limiting hole 64 and extension limiting pin 48 is shown to be positioned within an extension limiting hole 70. As such, flexion limiting pin 46 is positioned to abut flexion limiting face 76 formed in the second end of second arm 32 when second arm 14 is moved in a first direction of pivotal movement relative to first arm 12 denoted by arrow 78, this position representing the flexion limit. Conversely, extension limiting pin 48 is positioned to abut extension limiting face 80 formed in the second end of second arm 32 when second arm 14 is moved in a second opposite direction of pivotal movement relative to first arm 12 denoted by arrow 82, this position representing the extension limit.

Flexion pin retention member 84 and extension pin retention member 86 are shown in association with flexion and extension limiting pins 46 and 48 respectively. Retention members 84 and 86 are substantially identical in structure. Accordingly, the structure of either member is described with reference to retention member 84. Retention member 84 is a flattened elongated strip of flexible material, such as certain plastics or metals having these properties, which is flexibly deformable in a direction away from the face of the first plate 52, but preferably not substantially deformable in the direction of elongation parallel to the face of the first plate 52. The central end of the retention member 88 has an aperture 90 formed therethrough and aligned with a central aperture of first plate 92, a central aperture of second arm 94, and a central aperture of the second plate (not shown). The above-recited apertures are sized to receive pivot pin 36 in this sequence and pivotally retain the pin 36. It is further noted that second end of first arm 30 also has apertures 95 formed therethrough to receive rivets 44 and fixably engage plates 38 and 40 with the remainder of first arm 12.

Retention member 84 extends from central aperture of the first plate 92 across face 52 a radial distance corresponding to the outer radial distance of holes 64 and 66. The outer radial end of retention member 96 is provided with a longitudinal slot 98 which is sized to receive the segment of the limiting pin 63 and slidably retain the segment 63 therein. Accordingly, both the first and second widened portions 56 and 60 have a width larger than the width of slot 98 to prevent segment 63 from disengaging slot 98. The length of slot 98 is such that the outermost end of slot 98 aligns with outer radial holes 64, 66 and the innermost end of slot 98 aligns with inner radial holes 68, 70.

Cover 50 is preferably formed from a rigid transparent plastic and has a circular shape in correspondence with plates 38 and 40 to substantially cover the face of first plate 52. Cover 50 has an opening 100 formed therein, for which a lid 102 formed from like material is provided. Lid 102 is sized to fit over opening 100 when lid 102 is in a closed position and to expose opening 100 when lid 102 is in an open position as shown in FIG. 2. Accordingly, lid 102 is selectively positionable between the open and closed positions. A wire hinge 104 pivotally connects lid 102 to cover 50 and enables repositioning of lid 102 relative to opening 100. Wire hinge 104 is retained in fixed engagement with lid 102 by means of tabs 106a, 106b, 106c, while wire hinge 104 is retained in slidable engagement with cover 50 by means of a track 108.

Rotatable mounting of cover 50 on the face of the first plate 52 is provided by means of a central aperture 110 formed through a mounting member of cover 112. Aperture 110 is sized to receive and retain pivot pin 36 in the same manner as apertures 90, 92, 94. Cover 50 and lid 102 are provided with a cooperative locking mechanism to selectively retain lid 102 in the closed position. The locking mechanism comprises recesses 114 formed on the opposite sides of opening 100 in the cover sidewall 116, cover looking tabs 118 adjacent recesses 114, a fulcrum 120 on mounting member 112, and lid locking tabs 122 formed on opposite sides of lid 102 to align with recesses 114 and cover locking tabs 118.

Figure 3A:
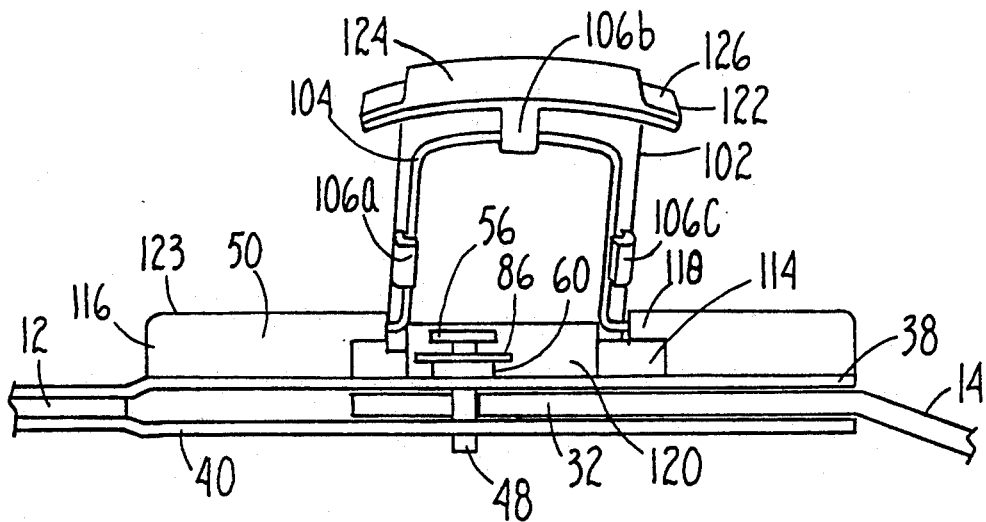
FIG. 3A is an elevational view of the hinged orthopedic brace of the present invention, wherein the lid is in the open position.
Figure 3B:
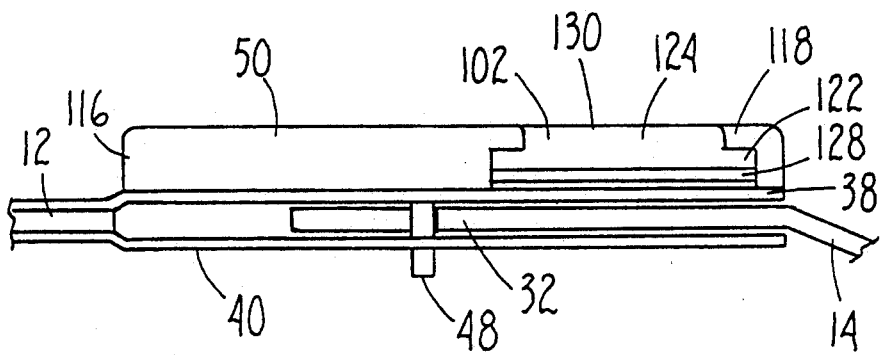
FIG. 3B is an elevational view of the hinged orthopedic brace of the present invention, wherein the lid is in the closed position.

Further details of the locking mechanism are shown with reference to FIGS. 3A and 3B. Referring initially to FIG. 3A, lid 102 is shown frontally in a partially open position for purposes of illustration, wherein lid 102 is rotated through an angle of about 45° from cover 50 to expose the first widened portion 56 of extension limiting pin 48. (It is noted that in the fully open position lid 102 is rotated through an angle of about 135° from cover 50.) To engage the locking mechanism, lid 102 is pivoted downward about wire hinge 104 toward opening 100, while sliding lid 102 forward relative to opening 100 by means of wire hinge 104 which is slidable within track 108. When lid 102 is flush with the top of cover 123, a sufficient downward force is applied to the front of lid 124 to flex lid 102 against fulcrum 120. Front 124 is depressed until lid locking tabs 122 become aligned with recesses 114 of cover 50. Lid 102 is then slid backward via wire hinge 104 within track 108 until front 124 is flush with the sidewall of cover 116.

With front 124 so positioned, the downward force on front 124 is withdrawn and front 124 elastically raises to an unflexed position, wherein recessed portions 126 of lid locking tabs 122 abut cover locking tabs 118 and a space 128 is provided between lid locking tabs 122 and first plate 38. This is the locked position of lid 102 as shown in FIG. 3B. Lid 102 is returned to the open position by following the same procedure in reverse order. It is noted that in the closed position, both the front 124 and top 130 of lid 102 are flush with cover 50 to provide the entire structure with a smooth snag-free surface.

It is further noted that lid 102 does not have sufficient clearance in the closed position to reside atop of first widened portion 56 or to pass over it when cover 50 is rotated. Accordingly, opening and closing of lid 102 is performed with lid 102 positioned away from limiting pins 46 and 48 as shown in FIG. 3B. Access to limiting pin 46 or 48 is provided by first opening lid 102 away from limiting pins 46 and 48, and then rotating cover 50 with lid 102 in the open position until opening 100 is positioned directly over limiting pin 46 or 48. Lid 102 is likewise closed by first rotating cover 50 with lid 102 in the open position until opening 100 is positioned away from limiting pin 46 or 48, and then returning lid 102 to the closed position.

METHOD OF OPERATION

Figure 4:
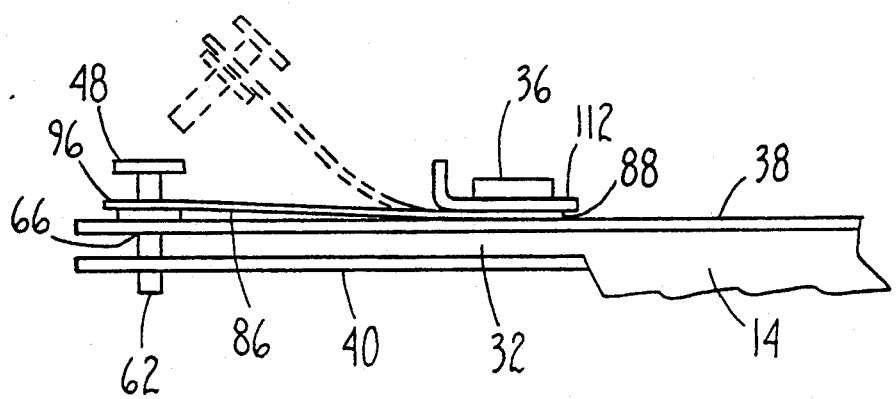
FIG. 4 is an elevational view of the hinged orthopedic brace of the present invention, wherein a limiting pin is shown positioned within a hole during use of the brace and positioned outside of a hole during adjustment of the brace.

Adjustment of the flexion and extension limits of brace 10 is described hereafter with reference to FIGS. 4 and 5. The preliminary steps in adjustment of the limits are first to displace lid 102 to the open position, thereby exposing opening 100, and subsequently to rotate cover 50 until opening 100 is over the desired limiting pin, such as limiting pin 48 shown in FIG. 4. Performance of the preliminary steps has been described above with reference to FIGS. 3A and 3B.

Referring initially to FIG. 4, wherein cover 50 has been substantially omitted for purposes of clarity, extension limiting pin 48 is shown positioned in a hole 66 with retention member 86 in an unstressed substantially linear configuration during use of the brace. When limiting pin 48 is withdrawn from hole 66, however, for repositioning of limiting pin 48 into a different hole, retention member 86 elastically deforms to a stressed arcuate configuration, as shown in phantom, caused by the displacement of the outer radial end 96 of retention member 86 while pivot pin 36 and mounting member 112 retain the central end 88 of the retention member 86 in place.

Once retention member 86 is in the stressed position, limiting pin 48 is freely pivotal by means of retention member 86 about pivot pin 36. Accordingly, retention member 86 is rotated until end of limiting pin 62 aligns with a different desired hole. Longitudinally sliding limiting pin 48 within retention member 86, as described previously, may further facilitate alignment of end 62 with a desired hole.

Figure 5A:
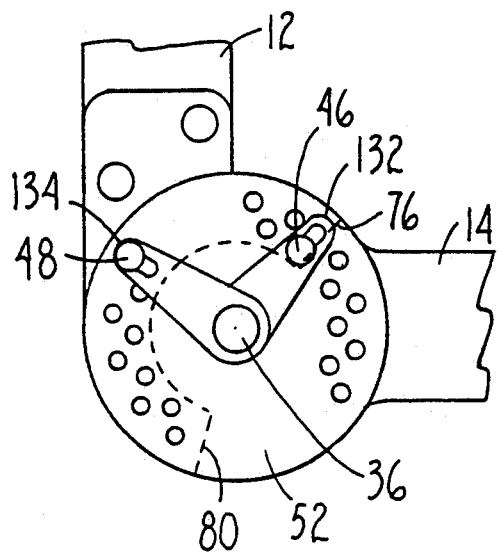
FIG. 5A is a top view of the hinged orthopedic brace of the present invention pivoted in a first direction to the flexion limit.
Figure 5B:
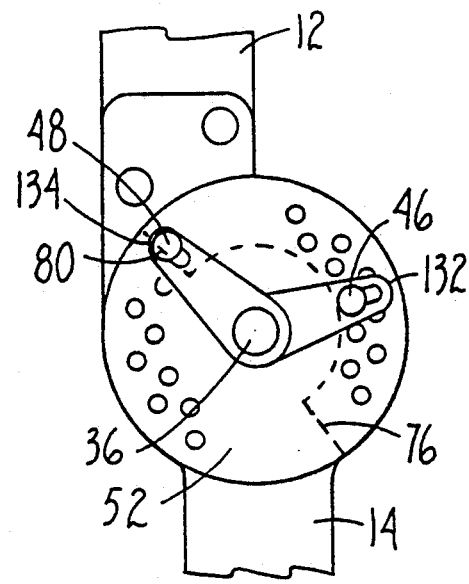
FIG. 5B is a top view of the hinged orthopedic brace of the present invention pivoted in a second direction to the extension limit.
Figure 5C:
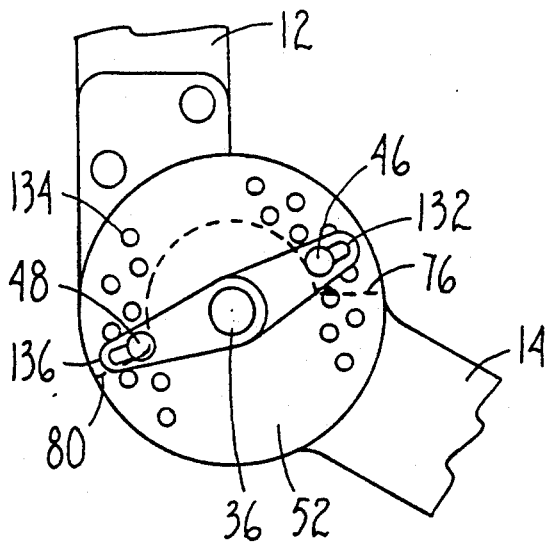
FIG. 5C is a top view of the hinged orthopedic brace of the present invention wherein the extension limit is readjusted from that of FIGS. 5A and 5B and the brace is pivoted in a first direction to the readjusted extension limit.

Referring now to FIGS. 5A, 5B, and 5C, adjustment of the extension limit is demonstrated by way of example. As in FIG. 4, cover 50 has been omitted from the above-listed figures for purposes of clarity. FIG. 5A initially shows flexion and extension limiting pins 46, 48 at first flexion and extension limits 132 and 134 respectively. At the first flexion limit 132, flexion limiting face 76 of second arm 14, shown in phantom, abuts flexion limiting pin 46 with arms 12, 14 and correspondingly the knee joint at a flexion angle of 90°. At the first extension limit 134, as shown in FIG. 5B, extension limiting face 80 abuts extension limiting pin 48 with arms 12 and 14, at an extension angle of 0°.

To adjust the first extension limit 134 to a second different extension limit 136 as shown in FIG. 5C, extension limiting pin 48 is removed from the first hole of FIGS. 5A and 5B and moved to the second hole in the manner described above with reference to FIG. 4. Repositioning of extension limiting pin 48 in the second hole thereby establishes the second extension limit 136 at an extension angle of 50°. It is apparent that any number of adjustments of the flexion or extension limits can be made in this manner by repositioning of flexion or extension limiting pins 46 and 48 respectively.

While the particular hinged orthopedic brace as herein shown and disclosed in detail is fully capable of obtaining the objects and providing the advantages hereinbefore stated, it is to be understood that the brace is merely illustrative of presently preferred embodiments of the invention and that other embodiments are possible within the scope of the present invention.

We claim:

1. An orthopedic hinge brace comprising:
a first arm having an end shaped-apart holes formed therethrough;
a second arm having an end;
arm connection means for pivotally connecting said end of said first arm to said end of said second arm;
limiting means for adjustably establishing a plurality of pivot limit positions for said second arm relative to said first arm, said limiting means comprising a limiting member, a first hole through said plate, and a second hole through said plate spaced a radial distance apart from said first hole, wherein said limiting member is insertable into said first hole to abut said second arm at a first pivot limit position when said second arm is pivoted in a first direction relative to said first arm, thereby limiting pivoting of said second arm past said first pivot limit position in said first direction, further wherein said limiting member removable from said first hole and insertable into said second hole to abut said second arm at a second pivot limit position when said second arm is pivoted in said first direction relative to said first arm, thereby limiting pivoting of said second arm past said second pivot limit position in said first direction; and
a retention member pivotally connected to said plate and having a longitudinal slot formed therethrough separately alignable with said first and second holes, wherein said limiting member is slidably positioned within said longitudinal slot.

2. An orthopedic hinge brace as recited in claim 1 wherein said arm connection means is a pivot pin extending through said plate and pivotally engaging said end of said second arm.

3. An orthopedic hinge brace as recited in claim 1 wherein said limiting member is a limiting pin having an elongated body with a first end, a second end, and a first widened portion between said first and second ends, wherein said first widened portion has a sufficiently large width to prevent passage through said first or second hole and said first end of said elongated body has a sufficiently small width to enable passage of said first end through said first or second hole.

4. An orthopedic hinge brace as recited in claim 3 wherein said elongated body has a second widened portion between said second end and said first widened portion and further wherein said elongated body is slidably positioned within said longitudinal slot between said first and second widened portions.

5. An orthopedic hinge brace as recited in claim 4 wherein said first and second widened portions have sufficiently large widths to prevent passage through said slot.

6. An orthopedic hinge brace as recited in claim 4 wherein said longitudinal slot is about equal in length to said radial distance.

7. An orthopedic hinge brace as recited in claim 1 wherein said retention member engages said arm connection means and said limiting member, and further wherein said arm connection means pivotally engages said plate.

8. An orthopedic hinge brace as recited in claim 1 wherein said retention member is formed from a flexible plastic.

9. An orthopedic hinge brace as recited in claim 1 wherein said about equal in length to said radial distance.

10. An orthopedic hinge brace comprising:
a first arm having an end shaped as a plate, said plate having a plurality of spaced-apart holes formed therethrough;
a second arm having an end;
means for pivotally mounting said end of said first arm to said end of said second arm;
limiting means for adjustably establishing a plurality of pivot limit positions for said second arm relative to said first arm, said limiting means comprising a limiting member, a first hole through said plate, and a second hole through said plate, wherein said limiting member is insertable into said first hole to abut said second arm at a first pivot limit position when said second arm is pivoted in a first direction relative to said first arm, thereby limiting pivoting of said second arm past said first pivot limit position in said first direction, further wherein said limiting member is removable from said first hole and insertable into said second hole to abut said second arm at a second pivot limit position when said second arm is pivoted in said first direction relative to said first arm, thereby limiting pivoting of said second arm past said second pivot limit position in said first direction; and
a cover positioned over said plate for selectively blocking removal of said limiting member from said first or second hole, wherein said cover has a lid and an opening, said lid having a closed position over said opening such that said cover substantially encloses said plate when said lid is in said closed position, thereby blocking removal of said limiting member from said first or second hole, and said lid further having an open position away from said opening, thereby enabling access to and removal of said limiting member from said first or second hole through said opening.

11. An orthopedic hinge brace as recited in claim 10 further comprising means for pivotally connecting said lid to said cover to enable movement of said lid between said open position and said closed position, wherein said cover is rotatably connected to said plate thereby enabling selective positioning of said opening over said first or second hole by rotation of said cover relative to said plate.

12. An orthopedic hinge brace comprising:
a first arm terminating in a pair of substantially parallel plates, the first plate of said pair having a plurality of spaced-apart holes formed therethrough, each of said holes in said first plate aligned with a hole formed through the second plate of said pair, said second plate thereby having a plurality of spaced-apart holes formed therethrough;
a second arm having an end positioned between said first and second plates;
arm connection means for pivotally connecting said first and second plates to said end of said second arm;
limiting means for adjustably establishing a plurality of pivot limit positions for said second arm relative to said first arm, said limiting means comprising a limiting member, a first pair of holes through said first and second plates, and a second pair of holes through said first and second plates, wherein said limiting member is insertable into said first pair of holes to abut said second arm at a first pivot limit position when said second arm is pivoted in a first direction relative to said first arm, thereby limiting pivoting of said second arm past said first pivot limit position in said first direction, further wherein said limiting member is removable from said first pair of holes and insertable into said second pair of holes to abut said second arm at a second pivot limit position when said second arm is pivoted in said first direction relative to said first arm, thereby limiting pivoting of said second arm past said second pivot limit position in said first direction;

limiting member connecting means for pivotally connecting said limiting member to said first and second pair of plates; and a cover positioned over said plate for selectively blocking removal of said limiting member from said first or second hole, wherein said cover has a lid and an opening, said lid having a closed position over said opening such that said cover substantially encloses said plate when said lid is in said closed position, thereby blocking removal of said limiting member from said first or second hole, and said lid further having an open position away from said opening, thereby enabling access to and removal of said limiting member from said first or second hole through said opening.

13. An orthopedic hinge brace as recited in claim 12 wherein said arm connection means is a pivot pin extending through said first plate and said end of said second arm to pivotally engage said second plate.

14. An orthopedic hinge brace as recited in claim 12 wherein said limiting member is a limiting pin having an elongated body with a first end, a second end, and a widened portion between said first and second ends, wherein said widened portion has a sufficiently large width to prevent passage through said first or second hole in said first plate and said first end of said elongated body has a sufficiently small width to enable passage of said first end through said first or second pair of holes in said first and second plates.

15. An orthopedic hinge brace as recited in claim 12 wherein said limiting member connecting means is a flexible retention member engaging said arm connection means and said limiting member, further wherein said arm connection means pivotally engages said first and second plates, said flexible retention member thereby pivotally connecting said limiting member to said first and second plates.

16. An orthopedic hinge brace as recited in claim 12 further comprising means for pivotally connecting said lid to said cover to enable movement of said lid between said open position and said closed position, wherein said cover is rotatably connected to said plate thereby enabling selective positioning of said opening over said first or second hole by rotation of said cover relative to said plate.

* * * * *

UNITED STATES PATENT AND TRADEMARK OFFICE
CERTIFICATE OF CORRECTION

PATENT NO. : 5,292,303
DATED : March 8, 1994
INVENTOR(S) : Charles A. Bastyr et al.

It is certified that error appears in the above-indentified patent and that said Letters Patent is hereby corrected as shown below:

Column 9, line 2:   delete "shaped-apart", and insert -- shaped as a plate, said plate having a plurality of spaced-apart--.

Signed and Sealed this

Fifteenth Day of November, 1994

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,292,303
DATED : March 8, 1994
INVENTOR(S) : Charles A. Bastyr, et al It is certified that error appears in the above-indentified patent and that said Letters Patent is hereby corrected as shown below:

Column 9, line 66: after "wherein said", insert -- longitudinal slot is --.

Signed and Sealed this

Thirteenth Day of June, 1995

Attest:

BRUCE LEHMAN

*Attesting Officer*     *Commissioner of Patents and Trademarks*